United States Patent [19]

Goeldner et al.

[11] Patent Number: 4,902,138

[45] Date of Patent: Feb. 20, 1990

[54] MEASURING COMPONENT CONCENTRATION IN A GAS BLEND

[75] Inventors: Heinz-Dieter Goeldner, Schwalbach/Ts.; Bertold Horn, Friedrichsdorf; Thomas Liedtke, Oberursel; Wolf-Ruediger Marx, Bad Vilbel/Gronau; Werner Schaefer, Kronberg, all of Fed. Rep. of Germany

[73] Assignee: Hartmann & Braun AG, Frankfurt am Main, Fed. Rep. of Germany

[21] Appl. No.: 176,888

[22] Filed: Apr. 4, 1988

[30] Foreign Application Priority Data

Apr. 4, 1987 [DE] Fed. Rep. of Germany ....... 3711511

[51] Int. Cl.⁴ .................. G01N 31/00; G01N 25/18
[52] U.S. Cl. ..................................... 374/44; 73/27 R;
                                                73/204.25; 338/22 R
[58] Field of Search ................ 374/43, 135, 44;
                                          73/27 R, 25, 204.25

[56] References Cited
U.S. PATENT DOCUMENTS

| 3,444,739 | 5/1969 | Treharne | 374/133 X |
| 3,607,084 | 9/1971 | MacKey et al. | 73/27 R X |
| 3,616,677 | 11/1971 | Oppegaard | 73/27 R |
| 4,389,876 | 6/1983 | Szonntagh | 73/27 R |
| 4,594,879 | 6/1986 | Maeda et al. | 73/27 R |

FOREIGN PATENT DOCUMENTS 2952137 1/1982 Fed. Rep. of Germany .
3502440 7/1986 Fed. Rep. of Germany .

Primary Examiner—Daniel M. Yasich
Attorney, Agent, or Firm—Ralf H. Siegemund

[57] ABSTRACT

The thermal conductivity in a gas blend is measured in order to determine concentration using several different temperatures for the gas but the same sensor, which includes a Silicon carrier of a few hundred micrometers thick and being provided with an electrically insulating layer; carrying a sputtered on or vapor deposited, meandershaped thin film resistance; a pit in the carrier underneath the resistance and the insulating layer, there being one or more perforations in the insulation to permit access of gas to the interior of the pit; a cover plate made also of silicon and of comparable thickness dimensions as the carrier, and also having a pit of comparable dimensions as the first mentioned pit is disposed above the carrier so that said pits are aligned and constitute a common measuring chamber; and a diffusion channel in the cover plate for feeding a gas through diffusion so that the measuring chamber is defined by the communicating pits.

9 Claims, 1 Drawing Sheet

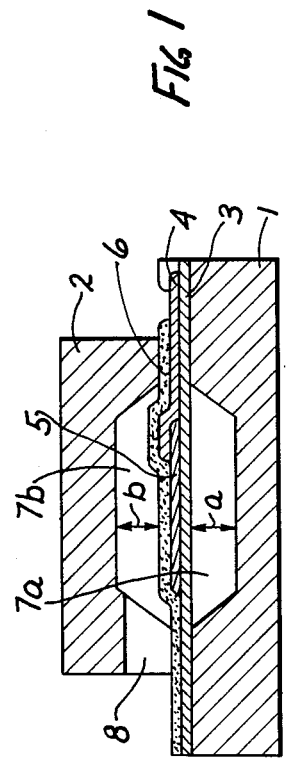
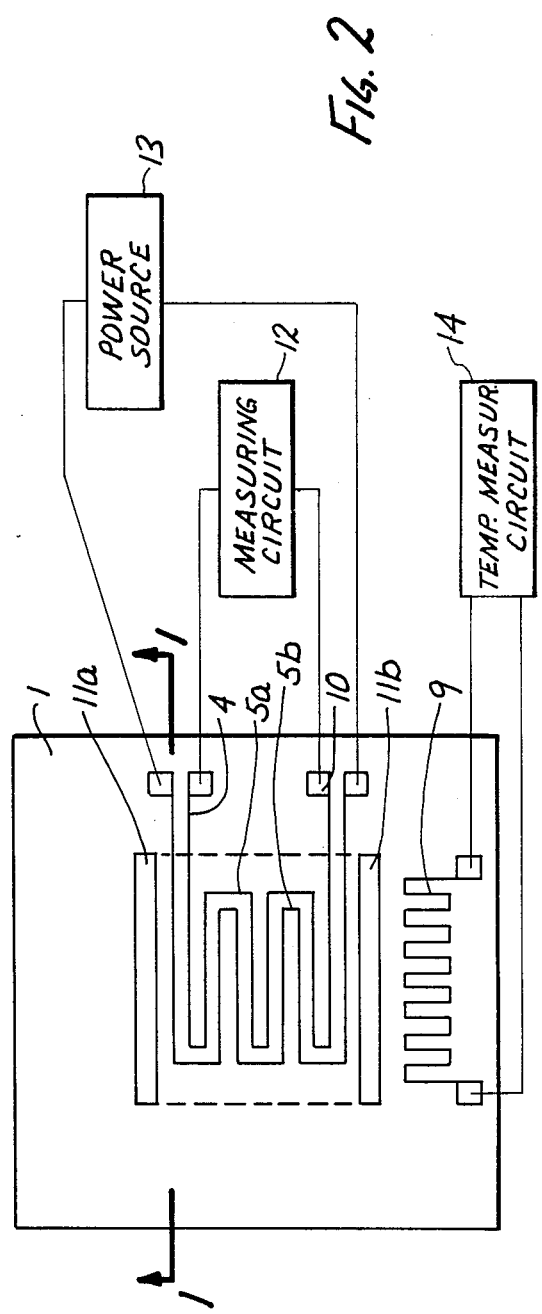

MEASURING COMPONENT CONCENTRATION IN A GAS BLEND

BACKGROUND OF THE INVENTION

The present application relates indirectly to measuring the gas concentration in a gas blend or mixture through directly measuring the thermal conductivity of that blend or mixture.

Generally, it is known to use differences in thermal conductivity, e.g different thermal conductivities of gases, to determine the consistency, constituents, and components of the gas. This approach that the thermal conductivity be measured at a particular gas temperature, or at least at an average temperature in those instances in which the temperature is, e.g. modulated, for reasons of signal processing. Only binary blends can be determined as to their components under such conditions. In case another component, be it a known one or unknown will falsify the measurement signal.

For measuring thermal conductivity by means of analyzers the following principles are being used at this time. A resistive heater is uses as a source for thermal energy, and by means of a particular electric current that element has it temperature raised vis-a-vis the respective environment. Heat is extracted through a heat conductive path of well defined geometry, and that conductive path is used to have heat transferred from that source to a heat sink of known temperature and under traversal of a particular path length of and within that gas. The heat transport from source to sink extracts a certain amount of energy from the source, and that flow and the resulting temperature conditions are used as an indicator and representation for the thermal conductivity of the gas occupying the space between source and sink. The heat is measured with an appropriate known method.

It is well known that the thermal conductivity of a gas is not constant but depends on its temperature. The dependence must be excluded through calibration and constancy conditions. The measuring cells are themselves subject to temperature control through an electronic circuit so that the measuring cells are being kept at a constant temperature. In addition, the average gas temperature is determined so that the temperature of the source itself should remain constant or at least reproducible.

A problem is posed by the conventional thermal conductivity sensing devices in that, on one hand, the particular path of the heat flow must be passed through continuously by gas. Also, a rather quick gas exchange is needed, and the flow of the gas, of course, determines but also interferes with the thermal transport, so that there is another parameter which provides possible interference with the measuring result.

German printed patent application 35 02 440 describes a method for compensating the measurement for the gas flow. German patent 29 52 137 describes a measuring cell wherein the gas is not subject to flow into and out of the area of measurement, but there is exchange through diffusion. In this case, the volume for the chamber in the gas path is relatively large so that the gas exchange in the measuring chamber may be too slow for certain tasks.

DESCRIPTION OF THE INVENTION

It is an object of the present invention to provide a new and improved method and equipment for determining the gas concentration in a gas blend that is usable also in cases where more than two gases are included in the blend, and to provide a new sensor operating with the gas exchange of less than one second.

In accordance with the preferred embodiment of the present invention it is suggested to provide a carrier plate, made of Silicon of one or a few hundred micrometers thickness, which carries an insulating layer upon which thin film resistors are provided through sputtering or vapor depositing. The resistance having a meandering shape configuration. The carrier has been etched in the area of these resistances so that a pit obtains which establishes the lower part of the measuring chamber of the sensor. A cover plate of Silicon is provided which also has an etched pit defining the upper part of the chamber. Perforations in the insulation cause the two pits to communicate to establish a jag chamber. The cover plate has an opening which acts as diffusion channel to provide access to the measuring chamber. This cell is used to determine gas concentration through the measurement of the thermal conductivity, the thermal conductivity is measured at a number of different temperatures and the number being one less than the number of gas components expected to be determined, and the plurality of the resulting thermal conductivity values is then processed mathematically for purposes of solving nonlinear equations so as to determine the individual gas concentration.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 1 is a cross section, as indicated by line I—I in FIG. 2, through a sensor constructed in accordance with the preferred embodiment of the present invention in realization of the best mode thereof; and FIG. 2 is a top review of the sensor shown in FIG. 1 with a cover plate removed.

Proceeding now to the detailed description of the drawings, the sensor is comprised of a carrier plate 1 made of Silicon and a cover plate 2 made of Silicon each having a representative thickness of about 370 micrometers. This is a value quite customary for Silicon wafers in semiconductor technology. The two plates 1 and 2 are bonded together through an adhesive by means of soldering or by anodic bonding. The sensor, particularly the carrier plate 1, has dimensions of a square to cover an area of about $5 \times 5$ mm$^2$.

The carrier plate 1 carries an insulating layer 3 which has been deposited thereon by a method known under PECVD (plasma enhanced chemical vapor deposition). Meander-shaped thin film resistances 5a, 5b, and 9, preferably made of Ni or Pt, have been vapor deposited or sputtered onto the insulation layer 3. Basically the method includes employment of photolithography.

This layer 3 is made of $SiO_2$ (Silicon oxide) or $Si_3N_4$ (Silicon nitride) or both. In case both materials are used, layer 3 may be comprised either of a single blend layer or of multiple lamina in which, e.g. these two materials, alternate.

The thin film resistances 5a, 5b are connected to conductors 4 made of gold and being applied in the same manner as the Ni or Pt resistor. These connection conductors 4 lead to the connection areas or vane 10 which are likewise made of gold and are of sufficient size to have the sensor elements connected to external circuitry. These includes source 13 for powering the thin film resistor 5b and a circuit 12 extracting measuring signals from resistance 5a, the signals indicative of gas components concentrations. After these general remarks, it should be pointed out that the measuring element of the sensor is, in fact, established by two meander-interlooped thin film resistors 5a and 5b. One of them is used as a heating conductor and the other is the temperature dependent resistor. In addition, there is a temperature measuring resistor 9 connected to a circuitry for measuring the sensor temperature at large i.e. the ambient temperature generally.

Following the application of the measuring elements and of the various thin film layers and configurations, a suitable cover 6 is provided for purposes of protection and being less than one micrometer thick. This layer 6 may be similar to layer 3, and the examples stated above as to material and configuration, are applicable also here.

Previously, or through undercut technique pit 7a has been etched through an anisotropic etching medium such as potassium hydroxide (potash) lye. This pit has been created in the wafer material 1a, and has a depth a of about 100 micrometers, covering an area under the measuring elements 5a, 5b of about $1 \times 1$ mm$^2$. Analogously, a pit 7b has been etched in the cover plate 2 having a depth b which is also about 100 micrometers. It can be seen from FIG. 1 that the horizontal dimensions of pit 7b are about the same as those of pit 7a. However, in the case of pit 7b, there is no insulating layer nor is there any measuring element except that, of course, pit 7b is positioned to cover the measuring elements on carrier plate 1. 11a and 11b are perforations in the insulation 3, so that pits 7a and 7b communicate.

Plate 2 has additionally a narrow opening 8 which serves as a diffusion channel to permit gas to diffuse-flow into the measuring chamber, being established by the two pits 7a and 7b. The dimensions of the channel 8 are chosen so that, on one hand, a sufficiently large opening obtains in the measuring chamber, so that indeed a gas exchange through diffusion is possible at a rather rapid rate. On the other hand, movements outside the measuring chamber are to be blocked off by the narrow dimensions of the diffusion channel i.e. they are not supposed to be transmitted as convective movements into the interior of the chamber 7a-7b. It is clear that these are opposite constraints on the dimensions of channel 8. By way of example, it was found that the opening 8 should have a height of about 100 micrometers, while the length of channel 8 is about 1 mm and covers the same side area of the pit.

It was found that a gas exchange in chamber 7a-7b obtains within a few hundred milliseconds, without having the measurement of thermal conductivity interfered with by any kind of convective or other flow such as it exists possibly outside of the measuring area. The gas exchange in the lower pit 7a obtains through perforations 11a and 11b in the insulation layer 3. In order to make sure that etching obtains in the proper manner, the insulating layer 3 may be provided with additional perforations not shown in FIG. 2.

The inventive device permits the measurement of thermal conductivity of a gas blend, possibly using different gas temperatures, whereby it is possible to determine the concentration of individual gases with more than two components being included in the blend. Also, the detection of unknown components is made possible. In other words, the inventive structure permits the recognition of external interferences and sources of trouble. Therefore, this novel heat conductivity sensor considerably enlarges and enhances the fields of use.

It is of particular advantage to use the novel sensor for measuring the thermal conductivity of a gas blend at different gas temperatures, without having several sensors to be maintained at different temperature levels. Rather, the sensor as described can be used, even if there is a variation in the gas temperature, because the rapid response permits ready compensation of what was previously temperature errors. This means that the overall expenditure for complete measurement in general is reduced and most importantly, variations in several sensors on account of variations in drift are avoided!

A prerequisite for carrying out measurements with a single sensor is that the thermal time constant of the sensor, i.e. its relaxation time is sufficiently short, so that the sensor readjusts quickly to temperature variations. This is possible, owing to the very low mass concerned in heating and into measuring elements, and further owing to the low weight of the carrying membrane (only a few micrograms). Thus, the inventive sensor has a time constant in the range of milliseconds and can, indeed, be used for the stated objectives.

Another advantage of the sensor is that the utilization of a very thin carrier 3 for the measuring and heating elements 5a-5b and 9, any heat conduction through the gas is much larger than conduction through the material of the heating element itself or its carrier. This ensures a high sensitivity of the sensor vis-a-vis any changes in thermal conductivity of the surrounding gas. The low heat conduction of the system and through the thin membranes means that the heat conduction through the gas can be commensurately reduced, e.g. through a lower differential temperature of a heat source and heat sink and the means of the suitable geometry of the type illustrated. This means that the electrical losses of the sensor are below 10 mw for many different kinds of gases.

The illustrated sensor is suitable in conjunction and through combination with microelectronic components. The sensor itself is minituarized and processes gas volume below 1 microliter. Owing to the particular size of the opening 8 only diffusion is the operative phenomenon by means of which gas is exchanged between the exterior and the chambers 7a and 7b, there being no convective flow involved. The suitably chosen relationship of the size of the diffusion opening, on one hand, and the chamber volume, on the other hand, permits gas exchange below 100 milliseconds, without having to utilize, on one hand, convective flow, but without interference of the measurement by any convective flow.

The integrated temperature measuring resistor permits introduction of any electronic correction of any temperature variations at the sensor, if that correction is needed. The passivation of the sensor is done through the materials for the layers 3 and 6, using $SiO_2$ and/or $Si_3N_4$. This feature permits the utilization of the sensor in an environment wherein the gas components, or some of them, may have aggressive properties. The use of Silicon as raw material for the wafers 1 and 2 takes advantange of process techniques known from semiconductor manufacturing, and here the sputtering and vapor depositing technology is also included. Generally, these advantageous features refer to is the utilizaton of photolithogrphy, etching and passivation. All this together pemits economic manufacture of many sensors from a single Silicon wafer.

The known methods for measuring heat conductivity are usually limited to two components of a binary blend. For reasons above, and for reasons of a principle nature, more than two components cannot be adequately determined and processed with past methods. A way out of this unfortunate situation results from the fact that the heat conductivity of gases are generally a function of the gas temperature, and this functional relationship is different for different gases. The inventive method as practiced by means of the device illustrated, permits the measuring of the thermal conductivity of a gas blend of more than two components, if one processes the gas at different temperatures in order to use the differences in the conductivity versus temperature relation among the various components.

The thermal conductivity of gases is usually pressure independent, particularly in the range of the customary atmospheric pressure about $10^5$ Pa). Hence upon measuring the thermal conductivity of the gas blend, one does not measure absolute concentration, i.e. partial pressures, but only mutual relationships. If one obtains in fact n-1 ratios for n gas components one can readily see that only n-1 different gas temperatures are needed for a complete set of measurement.

Neither the conductivity of the gas blend nor the conversion of the conductivity into electric signal by means of sensor can be assumed to involve linear functions of individual gas components. For determining the concentration of an n component gas blend, one needs a solution of a nonlinear equation system which, in fact, includes n1 equations. See e.g. transport phenomena by R. B. Bird, W. E. Steward and E. N. Lightfoot, 1960, chapter 8, page 243 et seq, John Wiley, New York and London. Whether this particular equation system is subject to a solution and can, in fact, be solved depends on the differences in the temperature dependency of the thermal conductivity of the various components. It depends also on the number of components as well as on the accuracy of the individual measurements. From a practical point of view, one will be able to use this method to determine the concentration of many 3-component blends, and some 4-component blends. It is decisive that large fields of application are available here and exhausiveness in the field is not a prerequisite for practical utility of the inventive method and application of the equipment.

In addition to determining the concentration of each component of an n component gas blend one can use the measurement of the thermal conductivity at different temperatures in order to determine whether or not within a normal n component gas blend there happens to be an n+1 component which is otherwise unknown. Thus, one determines and checks whether or not the measuring values for the thermal conductivity for two different gas temperatures and under consideration of the known temperature dependency of two known componets, yields consistent results. If that is not the case the presence of an unknown component is justifiably postulated and may be identified through extensive further measurements.

This method will operate in all those cases where the temperature dependency of the unknown component is different from the temperature dependency of any of the known components, and if the temperature dependency of the unknown component is not a linear combination of the temperature dependency of the known components. The exceptions are is merely a theoretical situations. In practice, this similarity will never obtain in a binary blend with a third, unknown component. The matter of detection is really a matter of sensitivity, rather than of hypothetical parameter similarities.

A further unknown component in a binary blend is usually also detectible at a sensitivity level far below 1%. However, for determining a fourth unknown component in a blend that includes three known componets, there is a limit for detection which is relatively high and for many cases it will not be possible to adequately determine the presence of such a fourth component.

The invention is not limited to the embodiments described above but all changes and modifications thereof, not constituting departures from the spirit and scope of the invention, are intended to be included.

We claim:

1. Sensor for measuring the thermal conductivity in a gas blend in order to determine and measure concentration of components of and in that blend comprising:
   a Silicon carrier being a few hundred micrometers thick and being provided with an electrically insulating layer:
   a sputtered on or vapor deposited meander shaped thin film resistance on the insulating layer;
   a pit in said carrier underneath said resistance and said insulating layer, there being at least one perforation in the insulation layer to permit access of gas to the interior of the pit;
   a cover plate made also of Silicon of comparable thickness dimensions as the carrier and also having a pit of comparable dimensions as the first mentioned pit, the cover plate being disposed above said carrier so that said pits are aligned and constitute a common measuring chamber; and
   a diffusion channel in the cover plate for feeding a gas through diffusion to the measuring chamber is defined by said two communicating pits when taken together.

2. Sensor, as in claim 1, the insulation being one of the following, Silicon oxide Silicon nitride; a blend thereof; a multilayer stratum of both said Silicon compounds.

3. Sensor as in claim 1, said carrier plate being provided in addition with a temperature measuring resistor outside the area defined by said pits.

4. Sensor as in claim 1, including a protective layer above the thin film resistance having a thickness of about 1 micrometer.

5. Sensor as in claim 4, said protective layer being made of Silicon oxide or Silicon nitride, or a combination thereof.

6. Sensor as in claim 1, the pit in said cover plate being between 10 and 100 micrometers thick.

7. Method of determining concentrations of various components in a gas blend by means of measuring the thermal conductivity of the blend, comprising:
   the steps of measuring the thermal conductivity in the blend at a number of different temperatures, at least as many as one less than a number of components expected to be present; and
   using one and the same heat conductivity sensor for the measuring steps.

8. Method as in claim 7, using a sensor for measuring the thermal conductivity in a gas blend in order to determine and measure concentration of components of and in that blend comprising:
- a silicon carrier being a few hundred micrometers thick and being provided with an electrically insulating layer;
- a sputtered on or vapor deposited meander shaped thin film resistance on the insulating layer;
- a pit in said carrier underneath said resistance and said insulating layer, there being at least one perforation in the insulation layer to permit access of gas to the interior of the pit;
- a cover plate made also of Silicon of comparable thickness dimensions as the carrier and also having a pit of comparable dimensions as the first mentioned pit, the cover plate being disposed above said carrier so that said pits are aligned and constitute a common measuring chamber; and
- a diffusion channel in the cover plate for feeding a gas through diffusion to the measuring chamber is defined by said two communicating pits when taken together.

9. Method for measuring the thermal conductivity in a gas blend in order to determine and measure concentration of components of and in that blend comprising: the steps of
(i) producing a sensor being comprised of a Silicon carrier being a few hundred micrometers thick and being provided with an electrically insulating layer, there being a sputtered on or vapor deposited meander shaped thin film resistance on the insulating layer;
- a pit in said carrier underneath said resistance and said insulating layers, there being at least one perforation in the insulation to permit access of gas to the interior of the pit;
- a cover plate made also of Silicon of comparable thickness dimensions as the carrier and also having a pit of comparable dimensions as the first mentioned pit, the cover plate being disposed above said carrier so that said pits are aligned and constitute a common measuring chamber;
- a diffusion channel in the cover plate for feeding a gas through diffusion so that a measuring chamber is defined by the combined communicating pits; and
(ii) measuring the thermal conductivity in said blend at a number of different temperatures, using said sensor whereby for n different components at least n-1 different measurements are made at n-1 different temperatures.

* * * * *